United States Patent [19]

Siegel

[11] 4,448,783
[45] May 15, 1984

[54] SUBSTITUTED PYRAZOLINE, AND ITS USE IN TREATMENT OF GASTRO-INTESTINAL DISTURBANCES

[75] Inventor: Marvin I. Siegel, Chapel Hill, N.C.

[73] Assignee: Burroughs Wellcome Co., Research Triangle Park, N.C.

[21] Appl. No.: 378,514

[22] Filed: May 17, 1982

[51] Int. Cl.³ ............................................ A61K 31/415
[52] U.S. Cl. .................................................. 424/273 P
[58] Field of Search ..................................... 424/273 P

[56] References Cited

FOREIGN PATENT DOCUMENTS 0022578 1/1981 European Pat. Off. ........ 424/273 P
1324687 7/1973 United Kingdom ............ 424/273 P

OTHER PUBLICATIONS

*Journal of Medicinal and Pharmaceutical Chemistry*, vol. 1, No. 2, 1959, p. 121—Yale.
*Pharmaceutical Sciences*, 1980, Mack Publishing Company, Easton, Penna., pp. 860, 850 and 851.

*Primary Examiner*—Frederick E. Waddell
*Attorney, Agent, or Firm*—Donald Brown

[57] ABSTRACT

A method of treatment of secretory diarrhea in mammals including man, comprising administration of a non-toxic anti-diarrheal amount of a compound of formula (I),

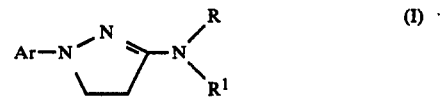

wherein
  Ar is 3-trifluoromethylphenyl,
  R is hydrogen and $R^1$ is selected from hydrogen and lower alkyl having 1 to 6 carbon atoms, or a pharmaceutically acceptable salt thereof in association with a pharmaceutically acceptable carrier therefor. The preferred formulations include those suitable for oral, rectal or parenteral administration, and the preferred dose is in the range of 0.5 to 500 mg/kg body weight of the compound, administered two or three times per day.

20 Claims, No Drawings

SUBSTITUTED PYRAZOLINE, AND ITS USE IN TREATMENT OF GASTRO-INTESTINAL DISTURBANCES

This invention relates to substituted pyrazolines, their preparation, pharmaceutical formulations containing them and to their use in medicine in a mammal, including man, as anti-diarrheal agents.

It has been found that the compounds of formula (I) and acid addition salts thereof can be used in medicine as anti-diarrheal agents.

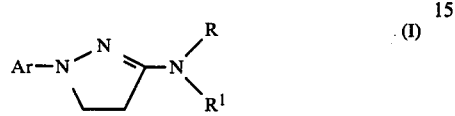

Ar is 3-trifluoromethylphenyl;
R is hydrogen; and
$R^1$ is selected from hydrogen and lower alkyl having 1 to 6 carbon atoms.
Example of compounds of formula (I) are:
3-methylamino-1-(3-trifluoromethylphenyl)-2-pyrazoline;
3-ethylamino-1-(3-trifluoromethylphenyl)-2-pyrazoline;
3-(n-propylamino)-1-(3-trifluoromethylphenyl)-2-pyrazoline;
3-(iso-propylamino)-1-(3-trifluoromethylphenyl)-2-pyrazoline;
3-(n-butylamino)-1-(3-trifluoromethylphenyl)-2-pyrazoline;
3-(sec-butylamino)-1-(3-trifluoromethylphenyl)-2-pyrazoline;
3-(tert-butylamino)-1-(3-trifluoromethylphenyl)-2-pyrazoline; and
3-amino-1-(3-trifluoromethylphenyl)-2-pyrazoline.

When used in medicine, the acid addition salts of the compounds of formula (I) should be both pharmacologically and pharmaceutically acceptable acid addition salts, but non-acceptable salts may conveniently be used to prepare the bases of such acceptable salts and are not excluded from the scope of this invention. Acceptable salts may be derived from organic acids, particularly dicarboxylic acids. Such pharmacologically and pharmaceutically acceptable salts include those prepared from the following acids: hydrochloric, hydrobromic, sulphuric, nitric, phosphoric, oxalic, fumaric, maleic, glycolic, salicyclic, succinic, p-toluenesulphonic, tartaric, acetic, citric, methanesulphonic, formic, benzoic, malonic, naphthalene-2-sulphonic and benzenesulphonic acids.

The compounds of formula (I) may be prepared by any method analogous to those known in the art, for example by the method of G. F. Duffin and J. D. Kendall in J.Chem. Soc. (1954), 408–415. Other methods include:

(1) A method for preparing a compound of formula (I) comprising cyclisation and elimination of water from a compound of formula (II).

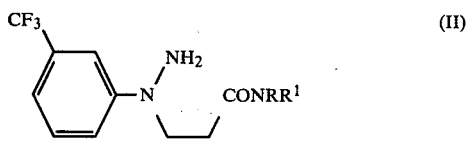

Suitable agents include phosphorous oxychloride ($POCl_3$).

The compound of formula (II) may itself be prepared by reaction of the corresponding compound of formula (III) with the corresponding compound of formula (IV)

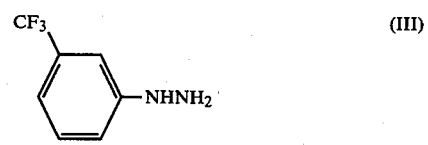

(2) A further method comprises reduction of a compound of formula (V)

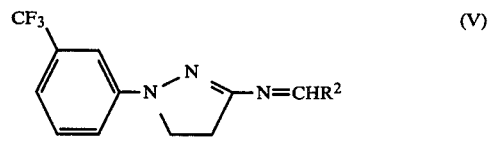

wherein $R^2$ is H or $C_{1-5}$ alkyl.

Suitable reducing agents are known to those skilled in the art and include sodium borohydride or another metallic reducing agent such as sodium cyanoborohydride; or by catalytic reduction using, for example, a catalyst such as platinum or palladium on carbon.

(3) A further method comprises reduction of a compound of formula (VI)

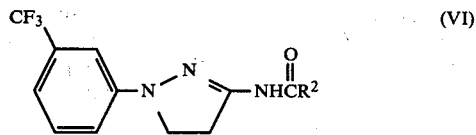

Suitable reducing agents are known to those skilled in the art and include diborane and lithium aluminium hydride.

The compounds of formula (I) may be used in the relief of secretory diarrhea in mammals including man.

The amount required of a compound of formula (I) (hereinafter referred to as the active ingredient) for therapeutic effect will, for course, vary with the route of administration and the mammal under treatment. A suitable dose of a compound of formula (I) for a mammal suffering from secretory diarrhea is 0.5 to 500 mg of base per kilogram body weight, the most preferred dosage being 0.5 to 50 mg/kg of mammal body weight for example 5 to 25 mg/kg, administered two or three times daily.

While it is possible for an active ingredient to be administered alone as the raw chemical, it is preferable to present it as a pharmaceutical formulation. Conveniently the active ingredient comprises from 0.1% to 99.9% by weight of the formulation. Conveniently unit doses of a formulation contain between 0.1 mg and 1 g, preferably between 0.5 and 50 mg, of the active ingredient.

The formulations, both for veterinary and for human medical use, of the present invention comprise an active ingredient in association with the pharmaceutically acceptable carrier(s) therefor and optionally other therapeutic ingredient(s). The carrier(s) must be 'acceptable' in the sense of being compatible with the other ingredients of the formulations and not deleterious to the recipient thereof.

The formulations include those in a form suitable for oral, rectal and parenteral (including subcutaneous, intramuscular and intravenous) administration.

The formulations may conveniently be presented in unit dosage form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

In addition to the aforementioned ingredients, the formulations of this invention may include one or more additional ingredients such as diluents, buffers, flavouring agents, binder, surface active agents, thickeners, lubricants, preservatives, e.g. methyl hydroxybenzoate (including anti-oxidants), emulsifying agents and the like.

Any other therapeutic ingredient may comprise one or more of the following: anti-biotic, anti-fungal and anti-viral agents. According to the present invention there is therefore provided a method for the prophylaxis or treatment of secretory diarrhea in a mammal, including man, comprising the administration to said mammal of a non-toxic effective anti-diarrheal amount of a compound of formula (I).

The following examples are provided by way of an illustration of the present invention and should in no way be construed as a limitation thereof. All temperatures indicated are in degrees Celsius.

EXAMPLE 1

Preparation of 3-methylamino-1-(3-trifluoromethylphenyl)-2-pyrazoline

A. Preparation of 3-Formamido-1-(3-trifluoromethylphenyl)-2-pyrazoline.

3-Amino-1-(3-trifluoromethylphenyl)-2-pyrazoline (1.907 g) (prepared as described in European Pat. No. 0022570) was dissolved in formic acid (20 ml). The solution was stirred at 60° and acetic anhydride (2.4 ml) added dropwise. The mixture was heated for 1 hour at 60° and then poured into water and stirred to decompose the residual excess anhydride. 3-Formamido-1-(3-trifluoromethylphenyl)-2-pyrazoline resulted as a crystalline solid m.p. 128°–129°.

B. Preparation of 3-methylamino-1-(3-trifluoromethylphenyl)-2-pyrazoline

3-Formamido-1-(3-trifluoromethylphenyl)-2-pyrazoline (2.4 g) was stirred with dry diethyl ether (60 ml) to produce a slurry which was gradually added to a stirred ice-cold suspension of lithium aluminum hydride (1.0 g) in dry diethyl ether (75 ml) under a nitrogen atmosphere. The addition took place over a period of about 20 minutes and was accompanied by a vigorous reaction. The final reaction mixture was stirred for a further 15 minutes and was then carefully and slowly decomposed by the addition of water (30 ml). The ethereal layer was then decanted off the aqueous sludge which was washed twice with diethyl ether. The combined ethereal solutions were dried over potassium carbonate, filtered and evaporated. The resulting 3-methylamino-1-(3-trifluoromethylphenyl)-2-pyrazoline was obtained as a colourless crystalline solid on trituration with benzene and recrystallization from light petroleum, yield 1.8 g, m.p. 93.1°. The hydrochloride was recrystallized by precipitation from methanol with ether and light petroleum m.p. 206°–207°.

EXAMPLES 2–4

The following compounds of formula (I) were prepared by a method analogous to the procedure of Example 1 using the indicated acid anhydride and chloroform in place of formic acid and acetic anhydride (Ex. 1 A.) and the indicated reducing agent/solvent (Ex. 1 B.).

| Ex. No. | $R^1$ | Acid Anhydride | Reducing Agent/Solvent | M.P. |
|---|---|---|---|---|
| 2 | $C_2H_5$ | Acetic | LiAlH$_4$/Tetrahydrofuran | 171.5° |
| 3 | $C_3H_7$ | Propionic | LiAlH$_4$/Diethyl ether | 151.2° |
| 4 | n-$C_4H_9$ | n-butyric | LiAlH$_4$/Diethyl ether | 173.4° |
| 5 | i-$C_4H_9$ | Isobutyric | LiAlH$_4$/Tetrahydrofuran | 167–168° |

EXAMPLE 6 TABLET

| | Per Tablet (mg) |
|---|---|
| 3-Methylamine-1-(3-trifluoromethylphenyl)-2-pyrazoline | 5.0 |
| Lactose | 82.0 |
| Starch | 10.0 |
| Povidone | 2.0 |

-continued

| | Per Tablet (mg) |
|---|---|
| Magnesium stimate | 1.0 |

The active ingredient, lactose and starch are mixed together and the mixture is granulated using a solution of povidone in purified water. The granules are dried and, after the addition of magnesium stearate, compressed to produce tablets, 100 mg per tablet.

EXAMPLE 7 INJECTION SOLUTION

| | Per Ampule |
|---|---|
| 3-Methylamino-1-(3-trifluoromethylphenyl)-2-pyrazoline | 10.0 mg |
| Water for injection, B.P. | q.s. to 1.0 ml |

The active ingredient was dissolved in about half of the water for injection and then made up to volume and sterilized by filtration. The resulting solution was distinfected into ampules under asceptic conditions, 1.0 ml per ampule.

EXAMPLE 8 SUPPOSITORIES

| | Per Suppository |
|---|---|
| 3-Methylamino-1-(3-trifluoromethylphenyl)-2-pyrazoline | 5.0 mg |
| Cocoa butter | q.s. to 2.0 g |

The cocoa butter is heated to melting and the active ingredient dispersed therein by thorough mixing. The mass is then formed into suppositories weighing 2.0 g each.

EXAMPLE 9

Measurement of transepithelial potential difference (PD) and short circuit current (Isc)

New Zealand white male rabbits (2–3 kg) were fed standard rabbit chow and water ad lib. Rabbits were killed by cervical dislocation, and the distal colon or ileum removed rapidly, opened along its mesenteric border, and rinsed clean of luminal contents with cold Ringer's solution containing, in mmol/liter NaCl, 114; KCl, 5; $NaH_2PO_4$, 0.3; $CaCl_2$, 1.25; $MgCl_2$, 1.1; and $NaHCO_3$, 25 (standard Ringer). Before use, tissues were maintained in ice-cold Ringer with 95% $O_2$/5% $CO_2$. The standard ringer solution also contained captopril ($5 \times 10^{-6}$ M) to inhibit bradykinin metabolism.

The serosa and two muscle layers were removed by placing a 10 cm strip of ileum, serosa up, on a Lucite plate, making a transverse cut through both external muscle layers with a razor blade, and stripping off the layers longitudinally.

Transepithelial electrical potential difference (PD), total conductance ($G_t$), and short circuit current (Isc) were measured as described by M. Field et al (A M J. Physiol, 220 1388–1396). Six pieces of mucosa were mounted in Ussing chambers (1.12 cm² cross-sectional area), and bathed with 8 ml of standard Ringer on each side. Solutions were circulated by gas lift and maintained at 37° C. in water jacketed reservoirs. Glucose, 10 μmol/ml, was added to the serosal medium, and an equimolar amount of mannitol was added to the mucosal medium.

The tissues were incubated with the compounds of formula (I) for 30 min prior to the addition of bradykinin ($1 \times 10^{-6}$ M). The compounds of formula (I) completely inhibited the response of the rabbit colon in vitro to bradykinin with $ED_{50}$ values as shown:

Compound of formula (I)

| $R^1$ | $ED_{50}$ (M) |
|---|---|
| H | $2 \times 10^{-4}$ |
| $CH_3$ | $5 \times 10^{-5}$ |

I claim:

1. A method of treatment or prophylaxis of secretory diarrhea in a mammal, including man, comprising the administration to said mammal of a non-toxic effective anti-secretory diarrheal amount of a compound of formula (I)

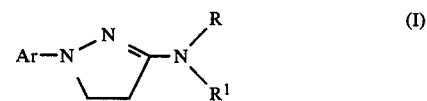

wherein
Ar is 3-trifluoromethylphenyl,
R is hydrogen and
$R^1$ is selected from hydrogen and lower alkyl having 1 to 6 carbon atoms, or a pharmaceutically acceptable salt thereof.

2. A method of treatment as claimed in claim 1 wherein the compound of formula (I) is in the form of a pharmaceutically acceptable salt thereof.

3. A method of treatment as claimed in claim 1 or claim 2 wherein the compound of formula (I) is in association with a pharmaceutically acceptable carrier therefor.

4. A method of treatment as claimed in claim 2 wherein the compound of formula (I) is in a form suitable for oral, rectal or parenteral administration.

5. A method of treatment as claimed in claim 2, wherein the compound of formula (I) is in unit dosage form.

6. A method of treatment as claimed in claim 1 or claim 2 which comprises the administration to said mammal of from 0.5 to 50 mg/kg body weight of the compound one to three times per day.

7. A method of treatment as claimed in claim 1 or claim 2 which comprises the administration to said mammal of from 5 to 25 mg/kg body weight of the compound one to three times per day.

8. A method of treatment as claimed in claim 1 or claim 2 wherein the compound of formula (I) is in association with a further therapeutic ingredient.

9. A method of treatment as claimed in claim 1 wherein the said mammal is human.

10. A method of treatment as claimed in claim 1 wherein $R^1$ is hyrogen or methyl.

11. A method of treatment as claimed in claim 6 wherein $R^1$ is hydrogen or methyl.

12. A method of treatment as claimed in claim 3 wherein $R^1$ is hydrogen or methyl.

13. A method of treatment as claimed in claim 4 wherein $R^1$ is hydrogen or methyl.

14. A method of treatment is claimed in claim 7 wherein $R^1$ is hydrogen or methyl.

15. A method of treatment is claimed in claim 9 wherein $R^1$ is hydrogen or methyl.

16. The method of claim 1 in which $R^1$ is hydrogen.

17. The method of claim 1 in which $R^1$ is methyl.

18. The method of claim 2 in which $R^1$ is hydrogen.

19. The method of claim 2 in which $R^1$ is methyl.

20. The method of claim 16, 17, 18 or 19 in which the compound is administered in a tablet or capsule.

* * * * *